US00PP35965P2

(12) United States Plant Patent
Hansen

(10) Patent No.: US PP35,965 P2
(45) Date of Patent: Jul. 2, 2024

(54) ***SEDUM* PLANT NAMED 'AFTER DARK'**

(50) Latin Name: ***Sedum* hybrid**
Varietal Denomination: After Dark

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 18/445,631

(22) Filed: Nov. 29, 2023

(51) Int. Cl.
*A01H 5/02* (2018.01)
*A01H 6/32* (2018.01)

(52) U.S. Cl.
USPC ..... Plt./479

(58) Field of Classification Search
USPC ..... Plt./479

CPC ... A01H 5/02; A01H 5/12; A01H 5/00; A01H 6/328; A01H 6/32
See application file for complete search history.

(56) References Cited

U.S. PATENT DOCUMENTS

PP35,725 P2 * 4/2024 Hansen ..... Plt./479

* cited by examiner

*Primary Examiner* — June Hwu

(57) ABSTRACT

A new and distinct ornamental perennial *Sedum* plant named 'After Dark' is characterized by tight-forming, medium-sized domed mounds with vertical stems producing deep-purplish-black leaves. The deep-purplish-black stems are highly branched, remain dense in the center, and resist lodging in the summer heat and rains. Numerous purplish-black flower buds open to show off garnet-colored flowers nearly completely covering the top of the plant and later display the dark red carpels. The new plant is useful for the landscape in containers, as specimens, or en masse.

1 Drawing Sheet

Botanical designation: *Sedum* hybrid.
Cultivar denomination: 'After Dark'.

STATEMENT REGARDING PRIOR DISCLOSURES UNDER 37 CFR 1.77(b)(6)

The claimed plant was first sold or offered for sale by Walters Gardens, Inc. to In the Country Gardens and Gifts on Dec. 1, 2022, by Walters Gardens, Inc., who obtained the plant and all information relating thereto, from the inventor. On Feb. 1, 2023, the plant was featured in a non-enabling disclosure of a brief description and photograph on a website operated by Walters Gardens, Inc. Subsequently, the new plant was advertised with a photo and brief description in the "Walters Gardens 2023-2024 Catalog." No plants of *Sedum* 'After Dark' have been sold or offered for sale in this country or anywhere in the world nor has any disclosure of the new plant been made more than one year prior to the filing date of this application, and such sale or disclosure within one year was either derived directly or indirectly from the inventor.

BACKGROUND OF THE INVENTION

The present invention relates to a new and distinct cultivar of *Sedum* plant, botanically known as *Sedum* and hereinafter referred to by the cultivar name 'After Dark' or the new plant.

The new *Sedum* plant is a selection of a planned breeding program conducted by the inventor, at a wholesale perennial nursery in Zeeland, Michigan, USA.

The new *Sedum* plant was selected as a single seedling from an insect pollination of the proprietary unnamed seedling referred to only by the breeder code 14-30-1 (not patented) at a wholesale perennial nursery in Zeeland, Michigan. The parent was placed in an isolation block next to seedlings and cultivars on about Sep. 1, 2015, and the seed was collected in the fall of the same year. *Sedum* 'After Dark' was assigned the breeder code number 15-19-11 to keep it separated from thousands of other seedlings of this and other crosses when it progressed through the initial trial phase in the fall of 2017. The selected single seedling clone line was originally selected for its strong stems, healthy, dense growth, colorful foliage and flowers, and intermediate traits between the female parent and those from the isolation block.

Asexual reproduction of *Sedum* 'After Dark' by division at a wholesale perennial nursery in Zeeland, Michigan, USA since October of 2017 and subsequent vegetative shoot tip cuttings has shown that the unique features of this new *Sedum* plant are stable and reproduced true to type in successive generations of asexual propagation.

SUMMARY OF THE INVENTION

Plants of *Sedum* 'After Dark' have not been observed under all possible environmental conditions. The phenotype may vary somewhat with variations in environment such as temperature, available water, fertility, and light intensity without, however, any variation in genotype.

The following traits have been repeatedly observed and are determined to comprise the unique characteristics of *Sedum* 'After Dark' and distinguish it as a new and distinct stonecrop plant unique from all other stonecrop plants known to the inventor:

1. Tight-forming, medium-sized, domed mounds with vertical stems;
2. Center stems remain erect throughout the growing season producing full habit;
3. Foliage is deep-purplish-black in high UV light exposure;
4. Numerous purplish-black flower buds develop into garnet-colored flower clusters completely covering the plant beginning in mid-August.
5. Flowers later take on a dark reddish color produced by the carpels.

In comparison with the female parent, the new plant has a slightly taller and less compact habit, stronger stems, darker foliage, and lighter rose-red flowers.

The nearest comparison varieties known to the inventor are: 'Night Embers' U.S. Plant Pat. No. 29,211, 'Back in Black' U.S. Plant Pat. No. 33,632, 'Black Jack' U.S. Plant Pat. No. 16,736, 'Night Light' U.S. Plant Pat. No. 34,272, 'Midnight Velvet' U.S. Plant Pat. No. 35,725, and 'Peach Pearls' (not patented).

'Night Embers' has a more open and taller habit and the foliage has a more brownish red overtone to the blackish-purple. 'Back in Black' is slightly taller in habit, with darker and wider foliage and the flowers produce light rose petals. 'Black Jack' is slightly taller and broader in habit, with darker burgundy foliage that is more susceptible to powdery mildew, and the broader flowers produce purplish-red to purplish-pink petals. 'Night Light' has a taller more erect habit, the foliage is smaller and olive-green with greyed purple, and the flowers are light yellow that mature to pink with deep-rose carpels. 'Midnight Velvet' has a slightly taller habit, narrower leaves, and the flower effect and the foliage has a more reddish tone. 'Peach Pearls' has a more upright and less mounded habit, with flowers that begin creamy-colored and the carpels develop to more bronzy red with seed.

BRIEF DESCRIPTION OF THE DRAWINGS

The drawings of the new plant demonstrate the unique traits and the overall appearance of *Sedum* 'After Dark'. The colors are as accurate as reasonably possible with color reproductions of this type. Variations in ambient light spectrum, source, and direction may cause the appearance of minor variations in color. The plants used in the photograph were four-year-old plants grown in an open, full-sun trial garden at a wholesale perennial nursery in Zeeland, Michigan with supplemental water and fertilizer when needed. No plant growth regulators or pinching have been used.

DETAILED BOTANICAL DESCRIPTION

Figure 1:
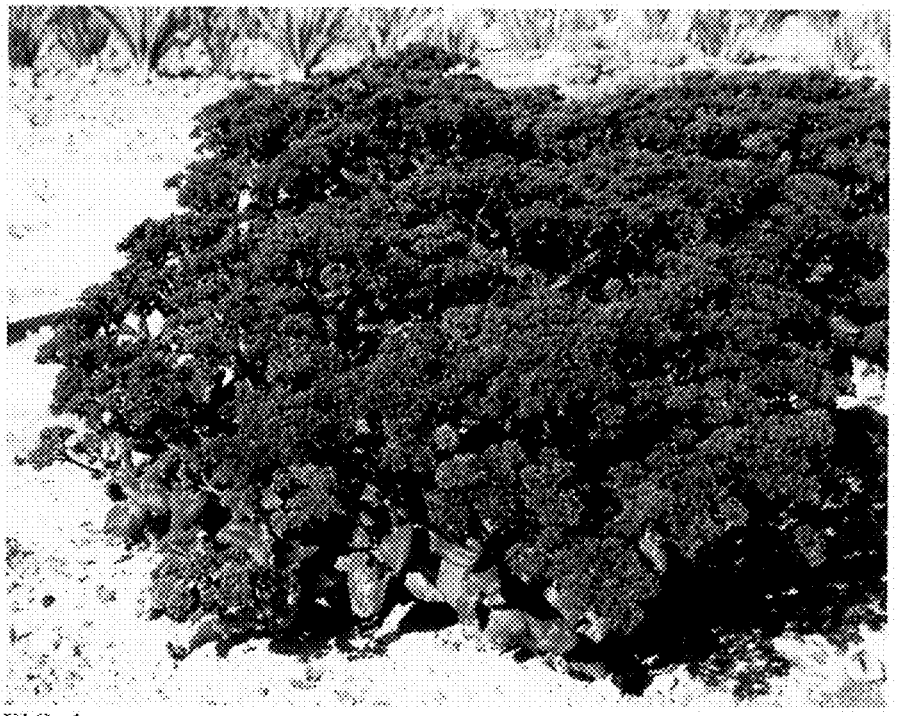
FIG. 1 shows the habit of the new plant with foliage in the early stages of flowering.
Figure 2:
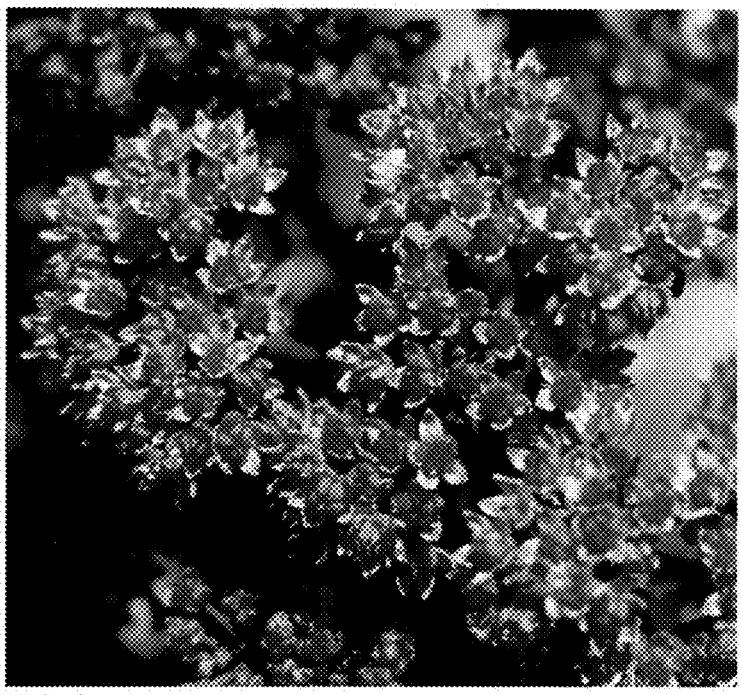
FIG. 2 shows a close-up of the flowers and buds of the new plant in mid-summer.

The following is a detailed description of two-year-old plants of the new cultivar as grown outdoors in a full sun trial plot and in a partially shaded greenhouse at a wholesale nursery in Zeeland, Michigan. No plant growth regulators have been used. Plants of the new cultivar have not been tested under all possible conditions. The phenotype may vary with changes in the environment, climate, and cultural conditions without a change in the genotype. The color reference is in accordance with the 2015 edition of The Royal Horticultural Society Colour Chart except where general color dictionary terms are used.

Botanical designation: *Sedum* hybrid.

Cultivar denomination: 'After Dark'.

Parentage: The female parent is an unnamed proprietary select seedling known only by the breeder code 14-30-1; the male parent is unnamed, but may have been any one of a number of other siblings, seedlings, or cultivars in the isolation block hybridizing area.

Asexual propagation: Stem tip cuttings and division.

Time to initiate roots: About two weeks.

Time to finish a 3.8-liter flowering container: About three months in the summer from a rooted 2.5 cm plug.

Root description: Thick, fleshy; freely branching; creamy white to light tan in color depending on soil composition.

Plant habit: Winter-hardy herbaceous perennial; upright mound; stiff upright stems; dense and full, not opening up in the center later in the season; flower heads densely and freely branching.

Growth rate: Moderately vigorous.

Plant size: About 40 cm tall and 56 cm wide in full flower.

Stems: Terete; glaucous; glabrous; to about 26.5 cm below first inflorescence branches, diameter at base to about 20 mm, average about 12 mm; heavily branched in distal inflorescence portion and proximally on exterior stems; about 8 cm long from base to initial branches on stems and about 26.5 cm from soil to first inflorescence branches on interior stems; to about 8 stems per plant and 7 branches per stem in lower exterior stems.

Stem color: Proximally or in shade nearest RHS 146B; distally in high light exposure variable, nearest RHS N186B and between RHS N77A and RHS N77B.

Lateral branches: To about 7 per stem; glaucous; glabrous; terete; primary branches to about 18 cm long before inflorescence and about 7 mm diameter at base.

Lateral branch color: Variable, nearest RHS N186B and between RHS N77A and RHS N77B.

Foliage: Ovate; opposite; simple; smooth; sarcous; glabrous and lightly glaucous on both surfaces; sessile; thick; apex acute; base cordate to rounded; margin crenate, 8 to 10 teeth; teeth to about 1 mm long and 4 mm wide; decreasing in size distally; attitude outward; to about 30 per stem, lower leaves not always persistent.

Foliage size: To about 7 cm long, 5.2 cm across, and 3 mm thick at midrib; average about 5.3 cm long, 3.3 cm across, and 3 mm thick; decreasing distally.

Foliage color: Adaxial young proximally nearest RHS NN137B, center and distally nearest RHS NN137B with slight blush nearest RHS N186B concentrated heavier toward margin, abaxial young between RHS N138C and RHS N138B; mature adaxial between RHS N186A and RHS 187A, abaxial between RHS N138C and RHS N138B variably blushed with between RHS 187A and RHS N186B.

Petiole: Leaves sessile.

Venation: Palmate; barely distinguishable; glabrous, glaucous, and slightly lustrous adaxial and abaxial; slightly costate abaxial.

Vein color: Adaxial midrib between RHS N186A and RHS 187A; abaxial midrib and one or two primary veins nearest RHS 146B with variable blushing of nearest RHS N186C stronger proximally; adaxial and abaxial secondary veins not obvious.

Flower buds about one day prior to opening: Ellipsoidal; apex acute; base truncate; about 4 mm long and about 3 mm diameter near middle.

Flower bud color: Petals nearest RHS 158C variably maculate to nearly solid in regions of high light exposure to between RHS 187C and RHS 187D; calyx nearest RHS N138D in lower light to RHS 189A with distal half strongly blushed with RHS N187A in high light.

Flower: Stellate, actinomorphic; perfect; complete; pentamerous; persistent; attitude upright to outwardly in terminal compound cymes.

Flower size: Size to about 6.5 mm across at petal apices and 4 mm tall, average about 6 mm across and 4 mm tall.

Flower number: To about 100 to 700 per branch, 2,500 to 5,500 flowers per stem, and 17,500 to 35,000 per plant.

Fragrance: None detected.

Flowering season: Beginning late-summer and continuing into fall in Zeeland, Michigan for about four weeks.

Longevity: Flower cymes remain effective for about four weeks on the plant and one to one and a half weeks as cut flowers; individual flowers, calyces, and persistent ovaries effective for about six weeks.

Inflorescence: To about 18 cm tall from below the first branch to the top, and about 20 cm across.

Petals: Typically, five; ovate to lanceolate; glabrous; acute apex; fused base; entire margin; slightly cupped; glabrous and slightly glaucous both abaxial; to about 4 mm long and 2 mm wide.

Petal color: Young flowers adaxial and abaxial nearest RHS 155B maculate with randomly concentrated semi-microscopic spots of nearest RHS 185C; before dehiscing adaxial transitioning to nearest RHS 186A proximally and the distal half nearest RHS 187B; before dehiscing abaxial proximal half between RHS 186C and RHS 186D distally nearest RHS 187B.

Calyx: With five sepals; campanulate to stellate; average about 3 mm across and 2 mm deep.

Sepals: Linear; narrowly acute apex; fused base; entire margin; slightly cupped; glabrous, and slightly lustrous both abaxial; adpressed to petals, to about 2 mm long beyond fusion and about 1 mm across at fusion.

Sepal color: Adaxial and abaxial nearest RHS N138D in lower light to RHS 189A with distal half strongly blushed with RHS N187A in high light.

Peduncles: Terete; glaucous, glabrous, becoming lustrous; stiff and flexible; freely and heavily branching; mostly upwardly in center of plant to slightly outwardly toward outside of plant; with branches and branchlets to about 45° above horizontal; to about 16 cm long and 7 mm diameter at base.

Peduncle color: Nearest RHS 146C, and with exposure to high ultraviolet light between RHS N186C and RHS 187A.

Pedicels: Cylindrical; glabrous; glaucous, becoming lustrous; strong and stiff, yet flexible; to about 4.5 mm long and 0.7 mm diameter; average about 3 mm long and 0.5 mm diameter.

Pedicel color: Between RHS N186C and RHS 187B.

Androecium: 10.

*Filament.*—Cylindrical; glabrous; lustrous; to about 2 mm long and 0.3 mm diameter; color nearest RHS NN155C.

*Anther.*—Ellipsoidal; about 0.7 mm long and 0.5 mm across; color nearest RHS 11A.

*Pollen.*—Abundant; color nearest RHS 11B.

Gynoecium: Typically, five; cylindrical, conical in distal one-third; to about 4 mm long and about 1.5 mm diameter near middle.

*Style.*—Conical; tapering distally with base truncate; about 1 mm long and 0.5 mm diameter at the point of attachment to ovary; glabrous; lustrous; color initially upon opening between RHS 58C and RHS 58D, progressing to between RHS 53B and RHS 53A at maturity.

*Stigma.*—Minute, acute; about 0.2 mm diameter and 0.2 mm long; color nearest RHS 53A at maturity.

*Ovary.*—Conical; acutely tapering at apex to style; base truncate; lustrous; about 4.0 mm long and 1.5 mm diameter; color initially upon opening between RHS 58C and RHS 58D, progressing to between RHS 53B and RHS 53A at maturity.

Fruit and seed: Not observed.

Growing conditions: Plants of the new *Sedum* 'After Dark' are xeromorphic and grow best with good drainage, full sun, and moderate to low fertility. 'After Dark' tolerates heavy rains and wind and is not prone to develop an open center later in the season as many other *Sedum* cultivars do that are known to the inventor.

Hardiness: The new plant is cold-hardy from USDA zones 3 to 9 and has tolerated temperatures of at least 35 degrees C.

Disease and pest resistance: The new plant has shown resistance to powdery mildew. Other pest and disease susceptibility, resistance, and tolerance outside that normal for *Sedum* is not known.

It is claimed:

1. A new and distinct perennial *Sedum* plant named 'After Dark' as herein described and illustrated.

* * * * *